(12) United States Patent
Hofler et al.

(10) Patent No.: US 6,677,132 B1
(45) Date of Patent: Jan. 13, 2004

(54) DEVICE AND METHOD FOR MONITORING AND CONTROLLING BIOLOGICALLY ACTIVE FLUIDS

(75) Inventors: Thomas Hofler, Munich (DE); Peter Holzhauer, Stuttgart (DE); Eckehard Walitza, Aalen (DE)

(73) Assignee: Fraunhofer-Gesellschaft zur Förderung der Angewandten-Forschung E.V. (DE)

( * ) Notice: Subject to any disclaimer, the term of this patent is extended or adjusted under 35 U.S.C. 154(b) by 0 days.

(21) Appl. No.: 10/009,882

(22) PCT Filed: May 12, 2000

(86) PCT No.: PCT/EP00/04289
§ 371 (c)(1),
(2), (4) Date: Mar. 28, 2002

(87) PCT Pub. No.: WO00/70078
PCT Pub. Date: Nov. 23, 2000

(30) Foreign Application Priority Data

May 12, 1999 (DE) .......................... 199 21 999

(51) Int. Cl.⁷ .......................... C12Q 1/02; C12M 1/00; C12M 1/36; C12M 1/34
(52) U.S. Cl. .................. 435/29; 435/283.1; 435/286.5; 435/286.6; 435/287.1
(58) Field of Search ............... 435/29, 283.1, 435/286.5, 286.6, 287.1

(56) References Cited

U.S. PATENT DOCUMENTS

| 3,731,522 | A | | 5/1973 | Mikesell .......................... 73/19 |
| 4,220,715 | A | | 9/1980 | Ahnell .......................... 435/34 |
| 5,224,051 | A | | 6/1993 | Johnson .................. 364/474.11 |
| 5,422,014 | A | | 6/1995 | Allen et al. .................. 210/743 |
| 5,614,378 | A | * | 3/1997 | Yang et al. .................... 435/41 |
| 5,702,951 | A | | 12/1997 | Bridger ...................... 436/62 |

FOREIGN PATENT DOCUMENTS

| DE | 4415444 | 11/1994 |
| DE | 4429809 | 2/1996 |
| DE | 19605753 | 9/1997 |

OTHER PUBLICATIONS

"An Oxygen Electrode–Based Assay of Catalase Activity as a Rapid Method for Estimating the Bacterial Content of Foods"; R.G. Kroll, et al.; *J. Appl. Bacteriol.*; 1989; 66(3); pp. 209–218; Abstract.

"A Biosensor System for the Determination of Cell Number of Enterococcus Seriolicida"; H. Endo, et al.; *Fisheries Science (Tokyo)*; 1996; vol. 62, No. 2; pp. 235–239; Abstract.

* cited by examiner

Primary Examiner—Louise N. Leary
(74) Attorney, Agent, or Firm—Ostrolenk, Faber, Gerb & Soffen, LLP

(57) ABSTRACT

The present invention relates to a device and a method for determining the concentration of organisms in a fluid, where metabolite parameters are recorded by means of a data acquisition unit and subsequently converted.

31 Claims, 3 Drawing Sheets

Figure 3A:
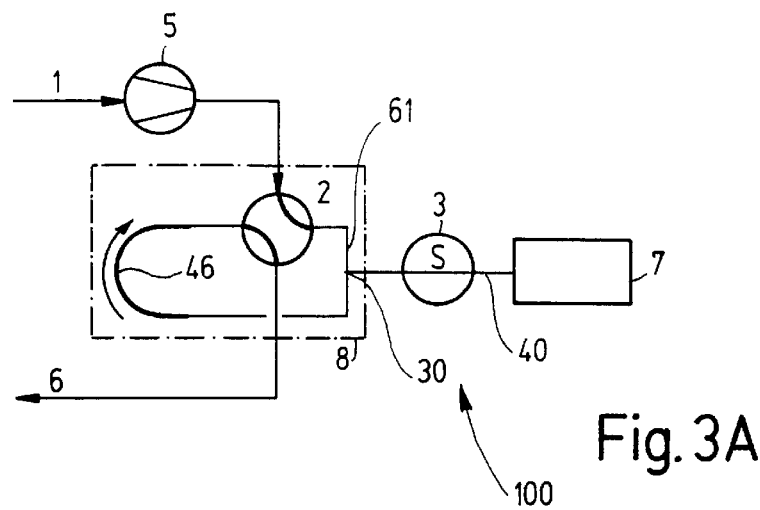

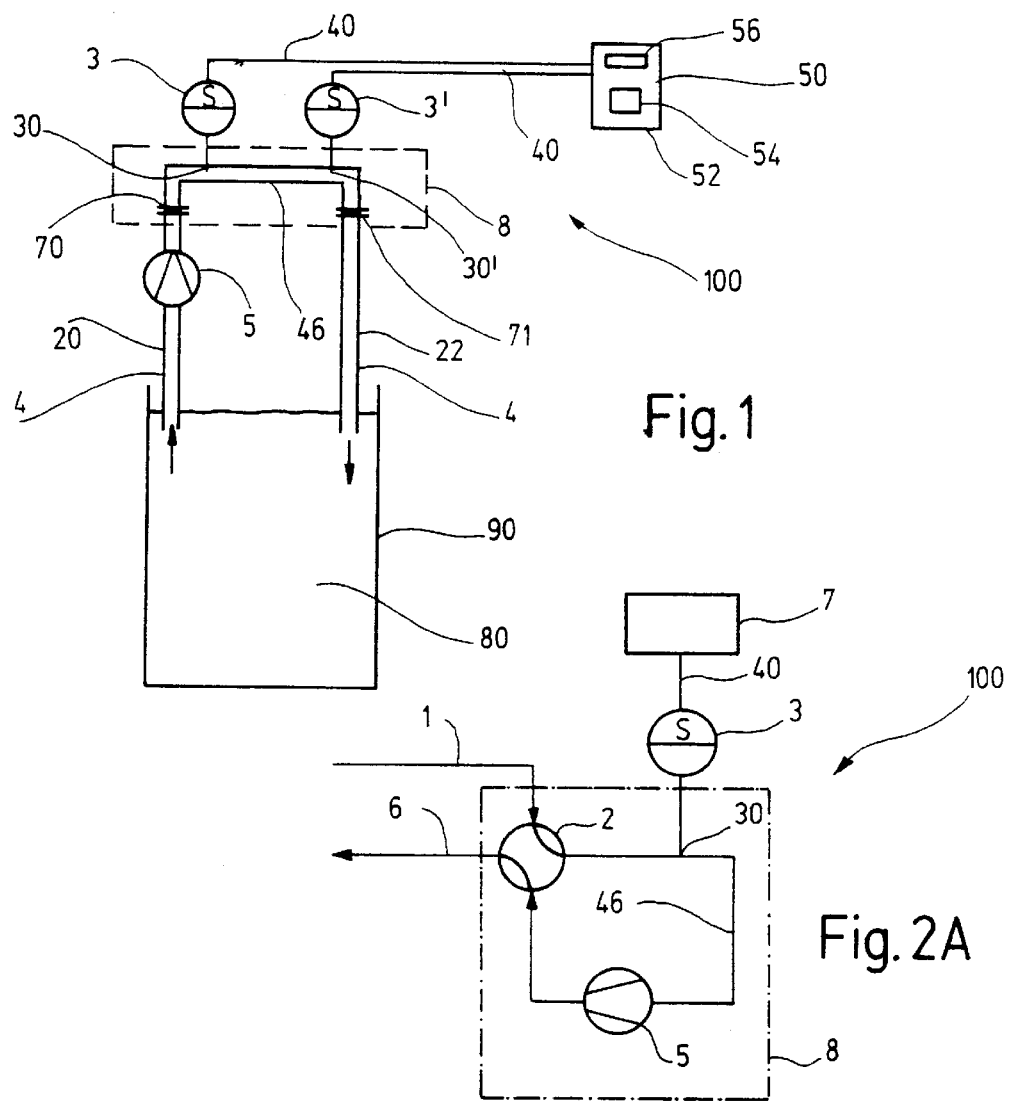
Fig. 1
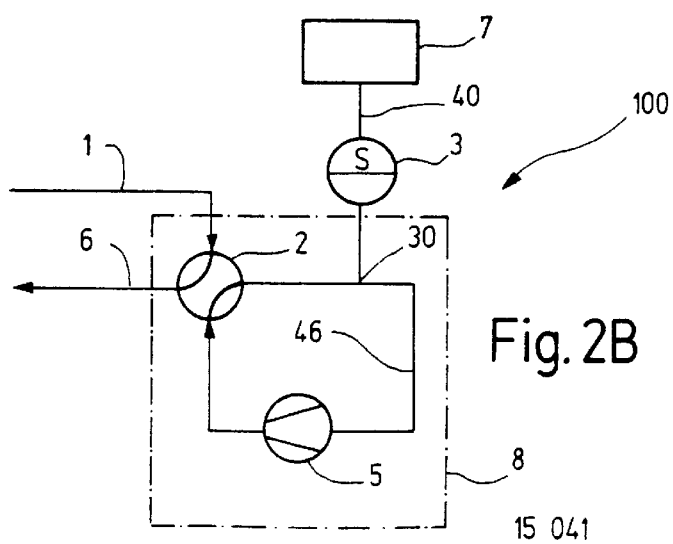
Fig. 2A
Fig. 2B

DEVICE AND METHOD FOR MONITORING AND CONTROLLING BIOLOGICALLY ACTIVE FLUIDS

This application is a 371 of PCT/EP00/04289, filed May 12, 2000, which claims priority to Germany 199 21 999.0, filed May 12, 1999.

DESCRIPTION

The invention relates to a device and a method for determining the concentration of organisms, in particular microorganisms, in a fluid.

The determination of the microbe content of fluids, generally expressed in colony-forming units per unit volume, preferably per milliliter (CFU/ml), normally takes place by inoculating nutrient media with the samples which have been taken, and counting the colonies. This procedure is time consuming and costly. In addition, online measurements of the microbe content, that is to say continuous measurements, are not possible.

In online measurement methods, normally only the biological activity of microorganisms is followed. This takes place, for example, by measuring the oxygen or carbon dioxide content, the pH or the concentration of fluorescent metabolic products. However, these methods do not produce a direct correlation, for example on the basis of the oxygen consumption, between metabolic activity and the number of microorganisms present.

Thus, for example, U.S. Pat. No. 5,224,051 describes an apparatus which measures inter alia the content of dissolved oxygen in cooling lubricants in order to obtain information about microorganisms. The apparatus does not, however, measure the oxygen consumption in a closed volume and, consequently, does not produce a correlation between temperature-dependent oxygen consumption and number of microbes in the solution either.

DE 44 29 809 A1 describes a method for the fully automatic control of fermentation processes for the production of alcoholic beverages in order to remove the heat of fermentation resulting from the alcoholic fermentation from the fermentation tanks. This entails measurement, outside the fermentation tanks, of the density of the liquid fermentation substrate, that is to say a metabolite parameter, but not the number of microorganisms involved in the fermentation.

DE 44 15 444 makes use of continuous measurement of the oxygen transfer rate to determine the physiological conditions in microbiological cultures. The oxygen transfer rate is measured from the fall in the oxygen partial pressure in the gas space using a sterilizable oxygen electrode. Direct calculation of the numbers of microbes from the oxygen consumption and the temperature is not disclosed.

U.S. Pat. No. 4,220,715 describes a method for detecting urinary tract infections in urine samples. This entails determination, on the basis of the oxygen consumption, of whether a preset threshold of microorganisms is exceeded in a urine sample. The method thus permits only qualitative and noncontinuous finding of the presence of certain microorganisms.

DE 196 05 753 A1 describes a method with which it is possible to measure the number of microbes per milliliter. However, the method requires very complicated apparatus because the microorganisms are firstly provided with a nutrient medium in order to achieve an optimal metabolism. In subsequent steps of the method, the intermediate and final products of metabolism are concentrated and fed into a chromatography system with detector and computer units.

None of the described methods enables the concentration of organisms, especially microorganisms, in a fluid to be determined accurately in a continuous, rapid and simple manner.

The technical problem on which the present invention is based is thus to provide a method and a device for carrying out the latter, by which continuous determination of the organism concentration in a fluid can take place in a rapid, simple and cost-effective manner, simultaneously achieving high precision.

The present invention solves the technical problem on which it is based by providing a method for the continuous determination of the concentration of organisms, in particular microorganisms, in a fluid which is present in a line section, where at least one data acquisition unit measures the time-dependent change in at least one metabolite parameter in the line filled with fluid, in particular in the part of the line, the line section, having the data acquisition unit or its sensor and the current organism concentration is found from the measurements by calculation based on a predetermined correlation between the change in the at least one metabolite parameter and the organism concentration. The change in the metabolite parameter measured by the data acquisition unit is preferably transferred to a data processing system and analyzed. A container which contains the fluid to be determined is preferably assigned to the line or line section. The line or line section assigned to the container represents a closed system for the fluid present and measured therein, that is to say a system which does not permit direct exchange of metabolites measured in the measurement zone with the—undefined—detour, where the line or the line section is continuously or periodically supplied from the container assigned thereto with fluid to be measured. The fluid from the container is thus generally not removed, for example using a scoop, from the container and transferred to a closed measurement system. On the contrary, the line is preferably in flow communication with the container, that is to say at least one of the openings of the line opens into the container and can receive fluid from there. The fluid present in the line is in a closed or quasi-closed system resulting from the residence time in the line section. Thus, according to the invention, the line section provides a closed system which makes a true measurement of changes in metabolites possible because of the residence time produced in the line section. A closed system is provided according to the invention inside a container or outside a container, it being possible to measure the change in metabolites directly in the fluid. The invention thus relates to a method for the continuous determination of the concentration of organisms in a in a line section, where a container containing the fluid to be measured is assigned to the line section and where the time-dependent change in at least one metabolite parameter in the closed system resulting from the residence time of the fluid in the line section is measured by at least one data acquisition unit. The invention accordingly provides for an organism-containing fluid which is present in a container and in a line preferably assigned thereto to be investigated in the line for a time-dependent, preferably additionally also temperature-dependent, change in at least one metabolite parameter. This entails the time-and, where appropriate, temperature-dependent change in at least one metabolite parameter, which has previously been determined to be suitable for one or more organism species, being determined by a data acquisition unit and the current organism concentration being calculated from the measurements on the basis of a predetermined correlation between the change in the at least one metabolite parameter and the organism concentration. The invention thus preferably provides for analysis, preferably in a data processing system, of the measurements after measuring the change in at least one metabolite parameter, where determination of the current organism concentration is made possible in the analysis by a previously determined computational association, also referred to as correlation hereinafter, between the change in the at least one measured metabolite parameter and the organism concentration. It is possible according to the invention with the aid of correlations found for specific organisms to find the concentration of the organisms as CFU/ml from the metabolite parameters which have been measured in a time-dependent and, where appropriate, temperature-dependent manner. The invention allows quasi- or semi-continuous and continuous, that is to say online, measurement of organism concentrations, in particular microorganism concentrations, or microbes in fluids in an advantageous manner.

The continuous measurement of microbes allowed according to the invention makes it possible to determine the organism concentrations in a particularly rapid and precise manner. In the conventional determination of microbes by plating out on nutrient media and counting the colony-forming units, the result is usually not available until after one or two days. By contrast, the result of measurement and analysis in the online procedure according to the invention—preferably stated as colony-forming units per milliliter (CFU/ml)—is available for example after only 5 to 240 minutes, preferably after 10 to 60 min. In addition, the invention has the advantage that no additional nutrient medium needs to be provided for the microorganisms. Concentration of the organisms is likewise unnecessary. The invention has the further advantage that only slightly complicated apparatus is involved and, in particular, it can also be carried out with microsystems technology, that is to say the line section which is required as reaction section and is also referred to as flow tube can, for example, also be in the form of an etched meander and on a glass substrate. The sensors, valves and pumps can likewise be executed with microsystems technology, and the flow tube preferably has a diameter of a few micrometers and a length of several centimeters.

It is thus possible with the procedure according to the invention to measure continuously or quasi-continuously the concentration of organisms, in particular microorganisms, as CFU/ml by, for example in the case of aerobic microbes, measuring in a flow tube or line section the consumption for example of oxygen ($O_2$) as metabolite parameter as a function of time and, preferably, also of temperature. The measurements are then converted by means of a previously determined correlation between $O_2$ consumption and microbe concentration into the microbe concentration present at that time.

In connection with the present invention, the term organisms means any type of living creature with metabolic activity, in particular microorganisms such as protozoa, bacteria, fungi, yeast, algae or lichens. Organisms of these types may be in unicellular or multicellular form, and they may also occur singly and/or form colonies. In a particularly preferred embodiment, the invention relates to the determination of the concentration of microorganisms such as Pseudomonas spec., *E. coli*, Lactobacillus spec., Bacillus spec., Leuconostoc spec., Clostridium spec., Saccharomyces spec., Sarcina spec., Candia spec., Streptococcus, Staphylococcus, Micrococcus, Methanobacterium, Methanococcus, Enterobacteriaceae, Enterococci, aerobic spore formers, *Pseudomonas aeruginosa, Bacillus subtilis* and Desulfotomaculum.

In connection with the present invention, a fluid means any type of liquid, gas with and without aerosol, for example air, suspension, emulsion, dispersion or mixtures thereof.

In connection with the invention, a liquid means any type of liquid which may potentially contain metabolically active organisms, for example effluent, culture liquids, media, liquids employed in food technology, the production of natural remedies, cosmetics, pharmacy and agriculture, in breweries, in fermentations and in medical technology, liquids involved in milk processing, in testing body fluids for microbes or else in the microbiological monitoring of humidifying devices in air-conditioning systems or in the control of affluents and effluents from sewage treatment plants or liquids used in the preparation of radiolabeled substances, in the production of energy and raw materials, in the quantitative determination of vitamins, amino acids and other compounds or in the isolation of intracellular substances (for example enzymes). In connection with the present invention, a liquid also means a liquid, in particular water, which contains microorganisms, for example through the introduction of microbe-containing gases, for example air, for example from air-conditioning systems, and is to be subjected to an analysis.

In connection with the present invention, a container having a line means any open or closed container which can be used to receive fluids according to the invention and additionally has a line in such a way that the latter is in flow communication with the container.

The term flow communication means in connection with the present invention that fluid flows from the container directly into the line assigned to the container, that fluid flows into the container directly from the line and/or that fluid can flow from the container directly into the line or from the line directly into the container. In a preferred embodiment, the line is connected by both its inlet opening and outlet opening directly to the container and is located, for example, outside or inside the container. It is, of course, also possible for the line to be connected by only one of its openings to the container, and to lead to or away from the container. In such a case the line would be designed as inlet or outlet line. It is also possible for the line not to be connected physically to the container directly but to be present for example inside the container without contact with the container walls or independently of a container.

In connection with the present invention, a line section means the component of the device according to the invention in which the time-dependent change in the metabolite parameter of the fluid present in the line section is measured by means of at least one data acquisition unit, and which, preferably designed in the form of tubing, has an inlet opening and an outlet opening. The line section can preferably be coupled by means of coupling units, for example valves, into existing line systems or lines of a container. The line section may also be an integral part, having at least one sensor, of a line. However, it is also possible to provide for the line section to be introduced into the fluid in the container and thus, as it were, represent in the terminology of the present invention the line of the container. Finally, it is also possible to provide for the line section not to be assigned to any container but for a fluid to be fed in any desired way to the line section of the device according to the invention so that the fluid can flow into the line section.

In connection with the present invention, a continuous measurement or determination means a determination in which the fluid flows continuously, that is to say without interruption, through the line and the line section having at least one data acquisition unit and the metabolite parameters are determined during this. The determination of the metabolite parameters and/or their analysis can moreover each take place continuously or at periodic intervals. A quasi-continuous or semi-continuous measurement or determination means in connection with the present invention a determination in which the fluid in the line and the line section having at least one data acquisition unit temporarily comes to rest and/or a flow reversal is brought about. In these cases too, the determination of the metabolite parameters and/or their analysis can take place continuously or at periodic intervals.

In connection with the present invention, a metabolite means a substance which is modified through the biological activity of an organism, in particular by a micro-organism; in particular, a substance which is consumed, that is to say a metabolic substrate, or produced, that is to say a metabolic product. Suitable as metabolic substrate and metabolic product are, for example, oxygen, methane, hydrogen, sulfide, nitrogen or a fermentation product such as ethanol, butanol, acetone, propanol, lactate, acetate, formate, butyrate, carbon dioxide, carbonate, ammonia, ammonium, nitrite, nitrate, hydrocarbons, aromatic hydrocarbons, metals, especially copper, iron, molybdenum and uranium, carbohydrates, especially starch, cellulose, pullulan, laminarin, melibiose, pectins, chitin and xylans, and/or hydrogen sulfide.

In connection with the present invention, a metabolic parameter means a datum which is quantitative in relation to the determined metabolite, for example the concentration of the metabolite, the pH of the liquid or its electrical conductivity. The redox potential may also be used as metabolite parameter. Such data on time-dependent determination of the metabolite parameter provide directly, for example concentration determination, or indirectly, for example redox potential, information about the consumption or production of the particular metabolite(s).

The metabolite concentration can, where appropriate, also be determined by optical measurement methods, for example UV or IR absorption, using thin- or thick-film sensors, semiconductor-based sensors, ion-selective electrodes or chromatographic measurement methods or ultrasonic measurement methods.

The invention provides in a preferred embodiment for the fluid to be in unbuffered form so that the pH and/or the conductivity can be used as metabolite parameter. However, it is self-evident that the invention also provides for the use of a buffered fluid, in which case the concentration of the metabolite(s) can be used, for example, as metabolite parameter.

In another preferred embodiment, the medium to be investigated can be removed unchanged through a diversion from the process to be investigated. It is possible in particular to produce a time lag after the diversion and before impingement on the measuring sensor or on the measuring probe. For example, the time lag can be varied, in particular through the length and/or diameter of a tube line, of a capillary or the like and the flow rate of the fluid.

In another embodiment, the line section can be bypassed, for example through valves, and the fluid can be circulated with the aid of a pump. The residence time, that is to say the time lag, is adjusted for example through the number of circulations or the duration of the bypass.

It is possible and preferred for a change in a parameter to be measured, which may correlate with the metabolism of the microorganisms, to take place on the route to the measuring probe.

In another preferred embodiment of the invention, the organism concentration, in particular microorganism concentration, is determined in a gas or gas mixture, for example air. This can take place according to the invention in the gas itself, where appropriate after concentration on membranes or filters, or by passing the gas or gas mixture through a liquid before carrying out the method described herein, so that the organisms present in the gas or gas mixture are washed out of the latter and accumulate in the liquid. The liquid is then transferred to the present method.

The invention provides in another preferred embodiment for the fluid to be passed during the measurement continuously through the line assigned to the container, in particular line section. This procedure is conditional on use of two sensors of a data acquisition unit in the line section.

A particularly preferred embodiment provides for the fluid to be rotated in the line in order in this way to ensure maximally uniform distribution of the at least one metabolite. This procedure is conditional on periodic uncoupling of the line section from the container, for example by means of one or more valves. The possibility of employing only one sensor of a data acquisition unit proves to be advantageous.

In another preferred embodiment, therefore, the invention provides for the measurement of the at least one metabolite parameter to take place using two data acquisition units connected in series or two sensors of a data acquisition unit, it being possible for the fluid to flow continuously through the line having the data acquisition unit. However, it is also possible to provide for the measurement to take place using one data acquisition unit or one sensor, in which case there is provision either of a preferably valve-controlled reversal of the direction of flow of the liquid in the line or a residence time of the fluid in the line. The determinations are then quasi-continuous, with the line or line section being uncoupled, preferably periodically, from the container.

In another preferred embodiment it is possible to provide for temperature control of the fluid, preferably in a range adapted to the particular species of organism, for example in a temperature range between 10° C. and 40° C.; in particular 30° C. to 35° C. for Pseudomonas spec. It is possible according to the invention to increase the measurement sensitivity by increasing the temperature and keeping this temperature constant, achieving a limit of detection with a limiting value of from 10 to 100 CFU/ml for Pseudomonas spec. for example at a temperature of from 30° C. to 35° C.

It is possible according to the invention in another preferred embodiment for gas mixtures or gases, for example air, to be passed into the fluid to be investigated if the content of dissolved gases, especially oxygen, is too low, and aerobic microbes are to be detected. It is, of course, also possible to supply other gases which allow detection of anaerobic organisms, for example in the medical/clinical sector, in sewage treatment plants and in the production of methane and acetate by carbonate reduction using methanogenic and acetogenic bacteria. It is possible where appropriate to provide in all the aforementioned embodiments a purification or sterilization procedure for the line section between individual measurement steps.

The invention also relates to a device for determining the concentration of organisms, especially micro-organisms, in a fluid, in particular for carrying out one of the aforementioned methods, where the device comprises a line, in particular a line section, a data processing system with a program for finding the organism concentration on the basis of a predetermined correlation between the change in at least one metabolite parameter and the organism concentration and at least one data acquisition unit which is disposed at least partly in or on the line. It is also, of course, possible for only part of the data acquisition unit, for example its sensor or measuring probe, to be disposed on or in the line section and transfer the measured data to the data acquisition unit which is, for example, integrated in the data processing system. In a preferred embodiment, the device according to the invention has a unit for determining the temperature in the line section, so that the method according to the invention can be carried out at controlled temperature and as a function of temperature.

The device according to the invention has a line section with, in each case, an inlet opening and an outlet opening, it being possible for these two openings or one of these two openings to have coupling units which make it possible to couple into a line of a container or into the container itself. However, it is also possible to provide for the line or the line section of the device to be immersed directly in the fluid in a container, or for the fluid to be introduced into the line section without providing a coupling directly to the container or onto one of its lines.

The program for finding the organism concentration has a correlation in the form of an algorithm which is written into a software program and which has been adapted for the particular analytical task, that is to say calculates the organism concentration or microbe count from the measured time-dependent change in one or more metabolite parameters. The correlation may also include a temperature dependence. The preconditions for constructing the program for finding the organism concentration is thus the position of a database from which it is possible to obtain a correlation between organism count and metabolite parameter as a function of time and, where appropriate, temperature. The organism concentration, in particular the microbe count, is found in a conventional way for producing these data sets, for example by plating out and counting on nutrient media. It is thus possible on the basis of conventionally obtained data about the organism concentration as a function of the temporal and, where appropriate, also temperature-dependent change in the metabolite parameter to obtain calibration curves and thus correlations which can be employed in the data processing system according to the invention.

In a particularly preferred embodiment, the data acquisition unit employed according to the invention is an $O_2$ data acquisition unit, a pH data acquisition unit, a conductivity data acquisition unit or a redox data acquisition unit. The data acquisition unit of the present invention comprises in each case at least one sensor or measuring probe which is immersed in the flow to be determined or is in contact therewith.

The metabolite concentration can also be determined where appropriate by devices for carrying out optical measurement methods, for example UV or IR absorption, or chromatographic measurement methods by means of thin- or thick-film sensors, semiconductor-based sensors or ion-selective electrodes or ultrasonic measurement methods.

The data found by means of the data acquisition unit or its sensor from the line section can be transferred, for example, via a data transfer cable to the data processing system. However, the invention also provides for remote data transfer from data acquisition unit to data processing system, for example by means of appropriate glass fiber-assisted systems, modems, bus systems, infrared equipment or radio.

In a preferred embodiment of the invention, the device additionally has at least one valve, for example a 4-way, 6-way valve or another multiway valve, preferably controlled via the data processing system. The valve may serve to couple the line section of the device according to the invention to a line of a container. It also serves to uncouple the fluid present in the line section from the line and the container, and the rotation and flow reversal where desired and necessary. The device may furthermore have at least one pump and a unit for temperature control. The pump may be switched off periodically in order to increase the residence time of the fluid in the line section and thus the accuracy of measurement.

In a preferred embodiment, the 4-way or 6-way valves may be omitted if a separate data acquisition unit is used for the inlet and outlet of the line section or flow tube in each case, or a data acquisition unit with two sensors is used.

The unit for temperature control serves to optimize the metabolic conditions of the organisms and can serve both for temperature control of the data acquisition unit, of the line or of the line section, of the pump and/or of the valve. The device and the method of the invention can, of course, also be carried out at ambient temperatures without temperature control.

In a particularly preferred embodiment, the line or the line section can be designed as tubing or as hollow fiber bundle, preferably with 10 to 10 000 fibers per bundle. Where the line section, which may also be designed as flow tube, is designed as tubing, it is possible to provide an internal diameter of from 0.5 to 100 mm, preferably 1 to 10 mm, with a length of from 0.05 to 50 m, preferably 5 to 20 m. Where the line section is designed as hollow fiber bundle, it is possible to provide an internal diameter of the hollow fibers of from 10 to 1 000 $\mu$m with a length of from 1 to 200 cm, preferably 1 to 40 cm. The use of hollow fibers has the advantage that the flow conditions can be optimized. The line section should preferably be designed for a fluid residence time which is accurately defined for each measurement task, and appropriate geometry, flow conditions and adsorption properties.

The device according to the invention can be constructed, for example, in such a way that the data processing system, for example based on a microprocessor, having a program for finding the organism concentration, where appropriate with a display device, is disposed in a housing and is connected by a data transfer cable to a line section which has at least one data acquisition unit and which has, where appropriate, one or more valves. The line section of this device is coupled into a system with a fluid to be analyzed, so that a defined line section, that is to say a line section with a defined geometry and defined flow properties, is available for acquisition of the measurements. The geometry of the line section preferably has dimensions such that settling and adhesion of the organisms cannot take place. It is, of course, also possible for the device to comprise a data processing system, a data transfer cable and a line section having a pump and having two sensors of one or two data acquisition units, the line section being simply immersed in the fluid in a container and the measurement being carried out with generation of a pump-driven flow in the line section.

The device according to the invention, that is to say the online acquisition system according to the invention, can also be designed by microsystems technology and/or as mobile diagnostic apparatus. Such a mobile, in particular wearable, device comprises a data processing system of the aforementioned type, at least one data acquisition unit with at least one sensor, which is disposed on or in a line section which is likewise provided. It is possible where appropriate for one or more valves to be provided on the line section.

It is also possible according to the invention with the aid of an upstream washer, that is to say a container having a liquid or a membrane or filter, to determine microbe counts in gas flows in which the gas is passed into the liquid or through the filter or the membrane. The measurement can take place directly on the microbes concentrated in this way on the filter or the membrane or, after detachment, in a liquid. It is moreover possible to control the sensitivity of detection via the concentration in the wash and the measurement temperature. In the gas wash provided according to the invention, the washing agent, for example water, or the membrane or the filter can be adapted to the microbe species, that is to say the organism species, to be determined, in order to maximize the measurement sensitivity.

In another preferred embodiment, a delay line can be provided. It is possible through the choice of the material of the line section which serves as delay line to exclude very substantially all interfering effects such as, for example, catalysis, the action of light and others which may adversely affect the correlation of said parameter with the metabolism of the microorganisms in an indeterminate and unintended manner.

In particular, the material of the line section and/or of the delay line may preferably consist of non-corrosive metals and metal alloys, inert plastics, ceramics and glasses. It is possible in particular to use only inert sealing materials, preferably welded connections.

It is possible in particular for sensors other than those provided for measuring the metabolism of the microorganisms also to be operatively connected to the device. The other sensors advantageously have no effect on the measurement of the sensor employed to measure the parameter correlating with the metabolism of the microorganisms, and particular preference is given to physical methods of measurement, such as, for example, density, refractive index, surface tension, turbidity, ultrasound, conductivity, pH, temperature and others. It is possible by combined analysis of at least two measured variables found to calculate otherwise inaccessible parameters of the fluid.

The arrangement of the measurement apparatuses can be chosen in particular so that interactions are excluded. It is possible and preferred for the device to be chemically and thermally sterilizable.

The invention is explained in more detail by means of exemplary embodiments and the relevant figures.

Figure 3B:
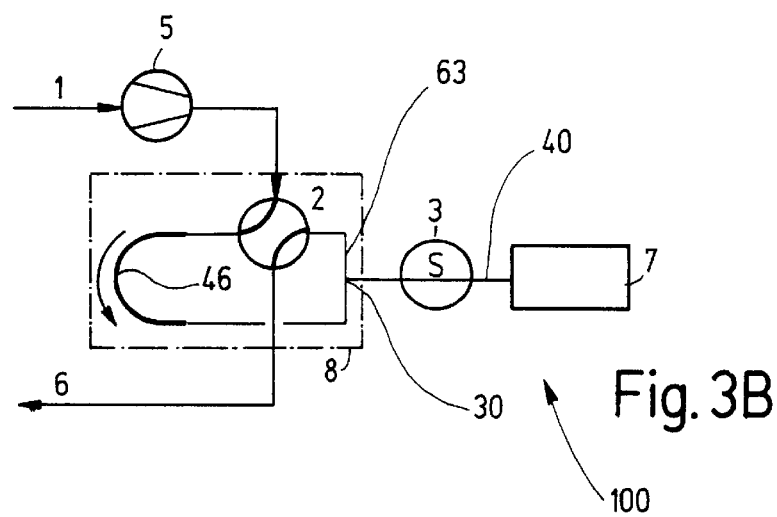

The figures show:

FIG. 1 diagrammatically a device according to the invention with two data acquisition units, FIGS. 2a and 2b diagrammatically a device according to the invention and the method carried out therewith for the quasi-continuous determination of the micro-organism concentration with 4-way valve and rotation, where FIG. 2a depicts the regeneration cycle and FIG. 2b depicts the measurement cycle, FIGS. 3a and 3b another embodiment of a device according to the invention and of the method carried outer therewith for the quasi-continuous determination of the micro-organism concentration with 4-way valve and flow reversal, where FIG. 3a depicts the measurement at the inlet of the flow tube and FIG. 3b depicts the measurement at the outlet of the flow tube.

Figure 4A:
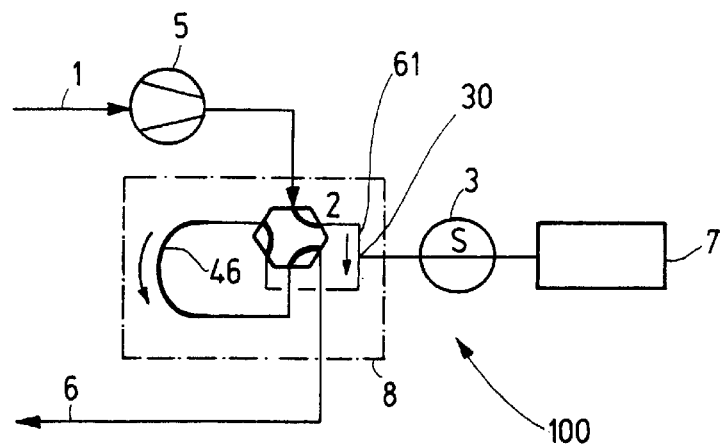
Figure 4B:
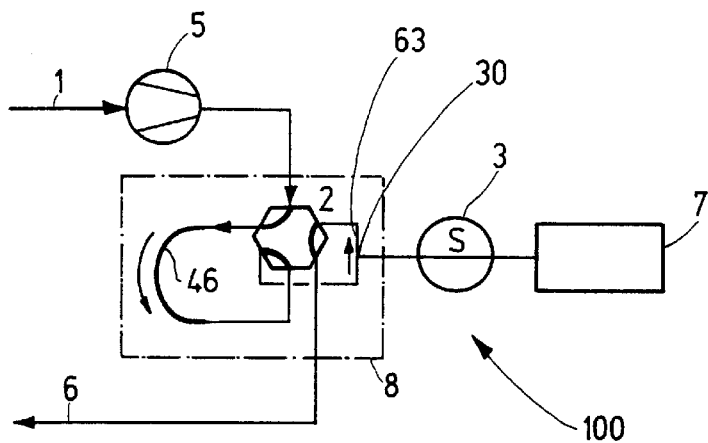

FIGS. 4a and 4b another embodiment of a device according to the invention and of the method carried out therewith for the quasi-continuous determination of the microorganism concentration with a 6-way valve without flow reversal in the line section, where FIG. 4a depicts the measurement at the inlet of the flow tube and FIG. 4b depicts the measurement at the outlet of the flow tube.

Figure 6:
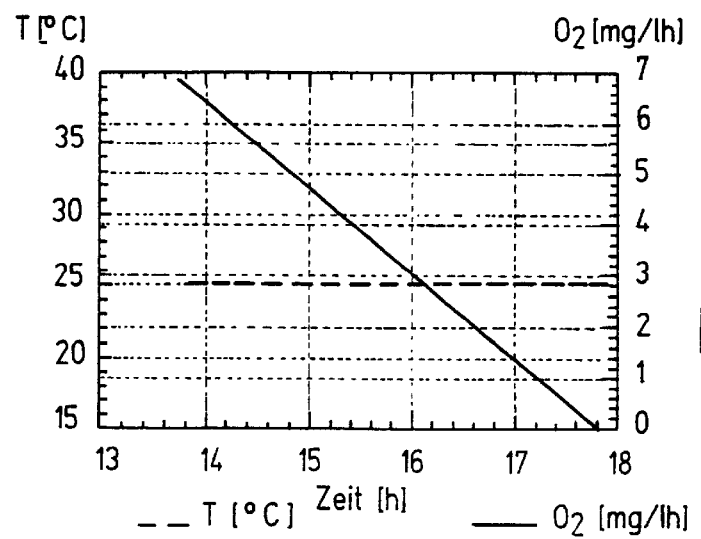
Figure 5:
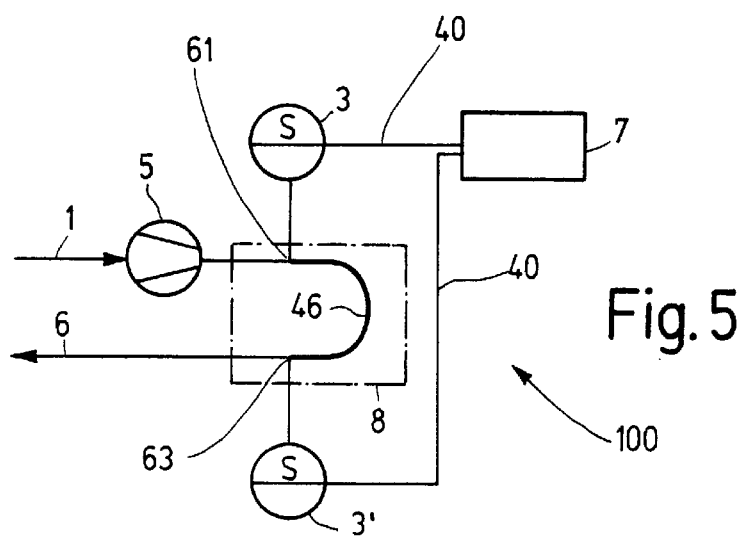

FIG. 5 another embodiment of the device according to the invention and of the method carried out therewith for the continuous determination of the micro-organism concentration with two data acquisition units and FIG. 6 typical changes in the oxygen content in a liquid containing microorganisms.

Identical reference numbers are used hereinafter for parts having identical construction and/or functions.

FIG. 1 shows a device 100 according to the invention which comprises a line section 46, two $O_2$ data acquisition units 3, 3' with in each case one measurement probe or sensor 30, 30' disposed in the line section 46, data transfer lines 40 and a data processing system 50. The two data acquisition units 3, 3' are each connected to the data processing system 50 via the data transfer lines 40. The two data acquisition units 3, 3' disposed on or in the line section 46 each have measurement probes 30, 30' which are disposed in the line section 46 and are able to make contact with the liquid 80 therein. One of the data acquisition units 3 is assigned to the sampling zone 20 of the line 4, while the other data acquisition unit 3' is assigned to the sample return 20 of the line 4. A lso depicted is the line 4 and the pump 5, which is assigned to the sampling zone 20, of the device 100 according to the invention. The line section 46 is integrated into the line 4 in flow communication by means of two liquid-tight couplings 70, 71. Finally, FIG. 1 depicts a container 90 with a liquid 80. A lso depicted is a temperature-control unit 8 which serves to keep the line section 46, in which the measuring probes 30 are disposed, at a constant temperature. The temperature control may, of course, additionally include other regions of the line 4, including the pump 5.

The data processing system 50 comprises a housing 52, a microprocessor 54 and a display device 56.

The microprocessor 54 of the data processing system 50 processes a program for finding the microorganism concentration, the microorganism concentration being determined by calculation from the time- and, where appropriate, temperature-dependently measured metabolite parameters transferred from the data acquisition units 3, 3' through the data transfer lines 40. For this purpose, the program has a correlation which calculates the organism concentration from the time- and, where appropriate, temperature-dependent change in a metabolite parameter. To determine this correlation it is initially necessary to create a database. This is described below for the oxygen concentration as metabolite parameter.

The procedure for finding the correlation between the time-dependent change in a metabolite parameter, in the present case the oxygen consumption, the microbe count and the temperature is as follows. A liquid 80 containing microbes is saturated with air, and the dependence of the oxygen consumption on the microbe count (CFU/ml) and the temperature is determined in the device 100 according to the invention. The test time is from 5 to 240 minutes, preferably 10 to 60 minutes. After each test it is possible if necessary to pass air through a frit into the solution until saturated. Samples which serve as reference are taken from the test system at the start of the test and at the end of the test for microbiological determination of the microbe count. The oxygen consumptions are each measured in the temperature range adapted to the species, for example between 10° C. and 40° C. FIG. 6 shows typical changes in the oxygen content in liquids containing microorganisms as a function of time for Pseudomonas spec. The liquid is a cooling lubricant emulsion containing Pseudomonas spec. This entails time-dependent measurement of the $O_2$ content, using the method depicted in FIG. 2, at a constant 25° C. The microorganisms result in a steady decline in the $O_2$ concentration. The microbe count detected microbiologically in this test is $3 \times 10^6$ CFU/ml. The oxygen consumption is 1.8 mg/lh at 25° C.

After the tests with the original solution, the test system is emptied and various dilutions are investigated. Once again, the oxygen consumptions are found between 10° C. and 40° C., and the microbe counts are determined by microbiological counting. In addition, the species of the microbes is identified by microbiological differentiation methods. A correlation is found from the data sets obtained in this way, that is to say oxygen consumption per unit time at a given temperature correlated with the microbiologically determined microbe counts. This correlation serves as algorithm for the online determination of the microbe counts.

The limit of detection for the microorganism concentration in the case of Pseudomonas spec. is at microbe counts of $>10^4$ CFU/ml for 20° C. and at microbe counts of $>10^2$ CFU/ml above 29° C. It is therefore particularly preferred according to the invention to measure the oxygen consumption in the liquid at elevated temperature in order thus to reduce the limit of detection.

It is possible for the finding of the correlation to be in part by self-learning, so that this is possible on site. For this purpose, temperature variations are carried out automatically in the temperature range adapted to the species, in particular a temperature range between 10° C. and 40° C., over a defined period. In parallel, samples are taken from the solution to be analyzed, and the microbe counts (CFU/ml) are determined thereon in the microbiological laboratory. The measurements obtained at the respective temperatures are then matched with the laboratory values through programmed-in analysis routines.

The mode of functioning of the device 100 depicted in FIG. 1 is as follows:

The microorganism-containing liquid 80 present in the container 90 is continuously pumped in one direction (arrow in FIG. 1) through the zone 20 of the line 4 by means of the pump 5. The two data acquisition units 3, 3' which are connected in series in the line section 46 and have measuring probes 30 determine, at a temperature predetermined by the temperature control 8, the oxygen consumption during the time required by the liquid to reach the sensor 30', which is assigned to the sample return zone 22 of the line 4, of the data acquisition unit 3' from the sensor 30, which is assigned to the sampling zone 20 of the line 4, of the data acquisition unit 3. On continuous measurement, the entry concentration of dissolved oxygen is measured with the data acquisition unit 3 and the exit concentration is measured with the data acquisition unit 3'. This results, owing to the line section geometry and owing to the flow rate, in a fixed residence time of the liquid. On discontinuous measurement, that is to say the pump is switched off periodically, firstly the data acquisition unit 3 measures the $O_2$ concentration at a given time, and, after a defined period has elapsed, the data acquisition unit 3' measures the $O_2$ concentration which has now been reduced due to the microorganism content. The time and temperature-dependent oxygen consumption found by the data acquisition units 3, 3' is passed as measured signal via the data transfer lines 40 to the data processing system 50, in particular to the data processing program present therein. The data processing program finds with the aid of the correlation previously stored therein the value of CFU/ml and displays it in the display device 56.

It is thus possible in this way for the value of CFU/ml to be determined online simply and precisely. It is necessary for this according to the invention merely to couple a device according to the invention with a defined line section 46, two data acquisition units assigned to the line section 46, and a data processing system into a container system containing the liquid to be determined, for example via previously existing lines or by introducing the line section 46 of the device 100 into the liquid 80 in the container 90 and then generating a liquid flow in the line section.

FIGS. 2a and 2b show in simplified diagrammatic representation another embodiment of the device according to the invention and of the method carried out therewith.

FIG. 2a shows a device 100 according to the invention composed of a data processing system 7, of a data acquisition unit 3 with the sensor 30, of a line section 46 of the undepicted line 4, into which section a pump 5 is integrated, and of a valve 2 which is designed as 4-way valve. The 4-way valve 2 also functions in this case as coupling between the line section 46 of the device 100 and the sampling line 1 and the sample return line 6, that is to say parts of the line 4 of the container. In FIG. 2a, the 4-way valve 2 is switched so that fresh liquid 80 can flow through the sampling line 1 into the line section 46 (regeneration cycle). In FIG. 2b, the 4-way valve 2 is switched so that the line section 46 represents a closed system and there is no connection through the sampling line 1 and the sample return line 6 to the undepicted container 90 (measurement cycle). The line section 46 can be designed as tubing, tube or hollow fiber bundle.

The device shown in FIG. 2 functions as follows: fresh liquid 80 from the undepicted container 90 is passed in the regeneration cycle through the sampling line 1 and the 4-way valve 2 into the line section 46. The 4-way valve 2 is then switched over, for example by signals from the data processing system 7, so that there is no connection of the line section 46 to the sampling and sample return lines 1, 6, and accordingly the line section 46 represents a closed system and the measurement cycle can take place. In this system, a first measurement of a metabolite parameter is carried out by the sensor 30, the value found is passed via the data transfer line 40 to the data processing system 50, and the liquid 80 in the line section 46 is rotated by the pump 5 for a given period. The rotation is necessary in order to avoid polarization at the sensor 30 of the data acquisition unit 3 and ensure good mixing of the liquid 80. At a defined time thereafter, the sensor 30 determines the same metabolite parameter once again, and the latter is likewise passed to the data processing system 7 for analysis by means of a correlation stored therein. After completion of the measurement cycle and switching over of the 4-way valve 2, the liquid 80 employed is passed through the sample return line 6 to the container 90, and fresh liquid is passed through the sampling line 1. At periodic intervals, the line section 46 is supplied with fresh liquid 80 by switching over the 4-way valve 2. The measurement time is determined by the switching intervals of the 4-way valve 2 which is controlled by the data processing system 7 or another unit. Time-dependent measurement is possible in this way. The pump 5, the line section 46, the 4-way valve 2 and the sensor 30 can be temperature-controlled by a temperature control 8 in order to generate optimal metabolic conditions for the microorganisms to be determined. The result is a quasi-continuous online measurement system.

FIG. 3 depicts another embodiment of a device according to the invention and of the method carried out therewith, but the measurement differs from the method depicted in FIG. 2 in taking place not in the periodically closed line but, instead, in a line section 46 which is continuously connected to the sampling line 1 and the sample return line 6. This is achieved by a flow reversal made possible by the 4-way valve 2 in the line section 46. The device 100 according to the invention thus has a data processing system 7, a data transfer line 40, a data acquisition unit 3 with sensor 30, a line section 46 and a 4-way valve 2. A pump 5 assigned to the sampling line 1, and a temperature control unit 8 are depicted. The 4-way valve 2 also represents the coupling of the device 100 to the sampling and sample return lines 1, 6 of the undepicted container 90.

FIGS. 3a and 3b depict the measurement with the aid of a line section 46, with a data acquisition unit 3 measuring, with the aid of a 4-way valve 2, either at the inlet 61 (see FIG. 3a) or the outlet 63 (see FIG. 3b) of the line section 46. Both the sampling line 1 and the sample return line 6 are connected to the undepicted container 90. The line section 46 is continuously supplied with fresh liquid 80 with the aid of the pump 5. When the 4-way valve 2 is switched over under the control of the data processing system 7, there is in each case a flow reversal in the line section 46. If, for example, the line section 46 is designed for a residence time of 10 minutes, when the data acquisition unit 3 is switched over from the inlet 61 to the outlet 63 of the line section 46 initially sample material, that is to say liquid 80, will pass through with a residence time of 10 minutes. The subsequent sample material from the line section 46 arrives with increasing residence time, resulting 10 minutes after the switchover in a residence time of 20 minutes for the liquid 80 transported back. The liquid following this then again arrives with a residence time of 10 minutes at the data acquisition unit 3. The liquid flow, the geometry of the line section 46 and of the sensor 30 are chosen so that optimal flow over the sensor 30 is ensured.

FIGS. 4a and 4b depict another embodiment of a device 100 according to the invention, and of the method carried out therewith, employing a 6-way valve 2 in place of the 4-way valve 2 in FIGS. 3a and 3b. It is possible with the aid of the 6-way valve 2 for the data acquisition unit 3 to determine with its sensor 30 the metabolite parameter either at the line entry 61 (see FIG. 4a) or line exit 63 (see FIG. 4b). The line section 46 is continuously supplied with fresh liquid 80 with the aid of a pump 5. The sampling line 1 as well as the sample return line 6 are connected to the container 90. Liquid 80 passes through the sampling line 1 and the pump 5 to the 6-way valve 2 and then initially into the inlet 61 of the line section 46. FIG. 4a shows that a first measurement is carried out there. After a defined time interval, the 6-way valve 2 controlled by the data processing system 7 is switched over and a second measurement is carried out (see FIG. 4b). It is possible by means of the switchover technique controlled by the data processing system 7, using a 6-way valve 2, to avoid a flow reversal in the line section 46. The liquid 80 arriving at the outlet 63 of the line section 46 has the same residence time in each case. The liquid flow and the geometry of the line and of the sensor 30 of the data acquisition unit 3 are chosen so that optimal flow over the sensor 30 is ensured. A residence time of the liquid 80 can be achieved by switching off the pump 5 or by other methods—such as closing a valve.

FIG. 5 shows another embodiment of the device 100 according to the invention and of the method carried out therewith, with the possibility of continuous measurement at inlet and outlet because of two data acquisition units 3, 3'. One data acquisition unit 3 with its sensor is located at the inlet 61 of the line section 46, that is to say the zone of the line section 46 facing the sampling line 1, whereas the other data acquisition unit 3' with its sensor is disposed in the exit zone 63 of the line section 46, that is to say the zone of the line section 46 facing the sample return line 6. The device 100 according to the invention thus has in this embodiment a line section 46, two data acquisition units 3, 3' and a data processing system 7, no valve being provided. The liquid flows, driven by the pump 5, from the sampling line 1 into the line section 46, undergoes determination of the metabolite parameter at its inlet zone 61, and then the liquid flows continuously onto the outlet zone 63 of the line section 46, in which another data acquisition unit 3', connected in series, carries out another determination of the metabolite parameter. The described liquid flow through the line section 46 is subjected continuously and simultaneously to a determination of the metabolite parameters at the two data acquisition units 3 and 3' so that differences, generated through the residence time of the liquid in the line section, in the metabolite parameters are passed continuously to the data processing system 7. It is then possible for the liquid to be passed back to the container 90 through the sample return line 6. The residence time can be varied by the flow tube geometry and the flow rate which can be adjusted by the pump 5. The measurements found are passed via the data transfer line 40 to the data processing system 7 and analyzed there by calculation by means of the stored program to determine the microorganism concentration, and are displayed as CFU/ml in a display device.

What is claimed is:

1. A method for the continuous determination of the concentration of organisms in a fluid present in a line section, where the time-dependent change of at least one metabolite parameter of a metabolite in the line section filled with the fluid is measured by means of at least one data acquisition unit and the concentration of organisms is found from the measured metabolite parameter by a calculation based on a predetermined correlation between the change of the metabolite parameter and the concentration of organisms.

2. A method as claimed in claim 1, where the line section is assigned to a container.

3. A method as claimed in claim 1, where the measured parameter is passed to a data processing system and analyzed.

4. A method as claimed in claim 1, characterized in that the organisms are microorganisms.

5. A method as claimed in claim 1, characterized in that the organisms occur unicellularly or multicellularly, singly and/or form colonies.

6. A method for the continuous determination of the concentration of organisms in a fluid present in a line section, where the time-dependent change of at least one metabolite parameter of a metabolite in the line section filled with the fluid is measured by means of at least one data acquisition unit and the concentration of organisms is found from the measured metabolite parameter by a calculation based on a predetermined correlation between the change of the metabolite parameter and the concentration of organisms, wherein the organisms are *E. coli*, Pseudomonas spec., Lactobacillus spec., Bacillus spec., Leuconostoc spec., clostridium spec., Saccharomyces spec., Sarcina spec., candida spec., Streptococcus, Staphylococcus, Enterobacteniaceae, Enterococci, aerobic spore formers, *Pseudomonas aeruginosa, Bacillus subtilis*, Micrococcus, Methanobacterium, Methanococcus and Desulfotomaculum.

7. A method as claimed in claim 1, where the metabolite is a substance which is changed by the organisms.

8. A method as claimed in claim 1, where the metabolite is one of a chemical compound and a chemical element.

9. A method as claimed in claim 1, where the measurement of the time-dependent change in the metabolite parameter takes place as a measurement of a change in a concentration of the metabolite of a pH of the fluid, of a conductivity of the fluid and/or of a redox potential of the fluid.

10. A method as claimed in claim 1, where the time-dependent change in the metabolite parameter is measured directly and/or indirectly with at least one data acquisition unit.

11. A method as claimed in claim 1, where a temperature-dependent measurement takes place.

12. A method as claimed in claim 1, where the measurement takes place while keeping the temperature constant.

13. A method for the continuous determination of the concentration of organisms in a fluid present in a line section, where the time-dependent change of at least one metabolite parameter of a metabolite in the line section filled with the fluid is measured by means of at least one data acquisition unit and the concentration of organisms is found from the measured metabolite parameter by a calculation based on a predetermined correlation between the change of the metabolite parameter and the concentration of organisms, wherein the line is decoupled from a container.

14. A method as claimed in claim 1, where the fluid flows continuously through the line.

15. A method for the continuous determination of the concentration of organisms in a fluid present in a line section, where the time-dependent change of at least one metabolite parameter of a metabolite in the line section filled with the fluid is measured by means of at least one data acquisition unit and the concentration of organisms is found from the measured metabolite parameter by a calculation based on a predetermined correlation between the change in of the metabolite parameter and the concentration of organisms, wherein the line is decoupled from a container and the fluid is rotated in the uncoupled line.

16. A method as claimed in claim 1, where a direction of flow of the fluid in the line is periodically reversed.

17. A method as claimed in claim 1, where the measurement is carried out quasi-continuously by means of at least one valve and at least one data acquisition unit.

18. A method for the continuous determination of the concentration of organisms in a fluid present in a line section, where the time-dependent change of at least one metabolite parameter of a metabolite in the line section filled with the fluid is measured by means of at least one data acquisition unit and the concentration of organisms is found from the measured metabolite parameter by a calculation based on a predetermined correlation between the change of the metabolite parameter and the concentration of organisms, wherein the measurement is carried out continuously by means of at least two data acquisition units.

19. A device for determining a concentration of organisms in a fluid, where the device comprises a line section, a data processing system with a program for finding the concentration of organisms on a basis of a predetermined correlation between a change in at least one metabolite parameter of a metabolite and the concentration of organisms, and at least one data acquisition unit which is at least partly disposed in or on the line section, and a sensor.

20. A device as claimed in claim 19, where the program for finding the concentration of organisms comprises an algorithm for determining the concentration of organisms as a function of a time-dependent change in the at least one metabolite parameter.

21. A device as claimed in claim 20, where the algorithm permits the concentration of organisms to be determined as a function of time and temperature.

22. A device as claimed in claim 19, where the line section has at least one valve.

23. A device as claimed in claim 19, where the data acquisition unit with the sensor comprises an oxygen data acquisition unit with the sensor.

24. A device as claimed in claim 19, where the line section is designed as tubing or a hollow fiber bundle, preferably with 10 to 10 000 fibers per bundle.

25. A device as claimed in claim 19, where at least one pump is assigned to the line section.

26. A device as claimed in claim 19, where the data processing system has a display device.

27. A device as claimed in claim 19, where the data processing system has a microprocessor.

28. A method as claimed in claim 7, wherein the metabolite is one of a metabolite substrate and a metabolic product.

29. A method as claimed in claim 8, wherein the one of the chemical compound and the chemical element includes at least one of carbon dioxide, nitrogen, hydrogen, sulfide, methane, a fermentation product such as ethanol, butanol, acetone, propanol, lactate, acetate, formate, butyrate, oxygen, carbonate, nitrite, nitrate, hydrogen sulfide, ammonium and ammonia.

30. A method as claimed in claim 12, where the temperature is kept constant in a range from 10° C. to 40° C.

31. A method as claimed in claim 13, where the line is decoupled from the container periodically.

* * * * *